United States Patent [19]

Yamaguchi

[11] 4,407,975

[45] Oct. 4, 1983

[54] POLYMERIC MEMBRANE HAVING MALEIC ANHYDRIDE RESIDUES

[75] Inventor: Tomohiko Yamaguchi, Yatake, Japan

[73] Assignee: Agency of Industrial Science and Technology, Tokyo, Japan

[21] Appl. No.: 352,863

[22] Filed: Feb. 26, 1982

[30] Foreign Application Priority Data

May 22, 1981 [JP] Japan .................................. 56-77485

[51] Int. Cl.$^3$ ............................................. B01J 47/12
[52] U.S. Cl. ....................................... 521/27; 521/28; 525/225
[58] Field of Search ..................... 521/27, 28; 525/225

[56] References Cited

U.S. PATENT DOCUMENTS 3,446,767  5/1967  Nolan .................................. 526/321
4,239,854 12/1980  Hirobara et al. ..................... 521/35

FOREIGN PATENT DOCUMENTS 1306472  2/1973  United Kingdom .................. 521/35

OTHER PUBLICATIONS

Chem. Abstract 120907R, vol. 82, 1975, Johansson et al.

Primary Examiner—Joseph L. Schofer
Assistant Examiner—Peter F. Kulkosky
Attorney, Agent, or Firm—Armstrong, Nikaido, Marmelstein & Kubovcik

[57] ABSTRACT

A polymeric membrane having maleic anhydride residues which comprises a blend of a maleic anhydride copolymer and a support polymer, said blend being partially cross-linked with a bifunctional cross-linking reagent. When hydrolyzed, this membrane turns into an ion exchange membrane or a membrane on which an enzyme is immobilized.

8 Claims, No Drawings

POLYMERIC MEMBRANE HAVING MALEIC ANHYDRIDE RESIDUES

BACKGROUND OF THE INVENTION

The present invention relates to a polymeric membrane having maleic anhydride residues, an ion exchange membrane derived from the membrane, and an enzyme immobilizing membrane.

The maleic anhydride copolymer is known as a reactive polymer because the maleic anhydride residues are reactive. The maleic anhydride copolymer, however, has not been put into practical use in the form of membrane because it hydrolyzes gradually in an aqueous solution into a water-soluble polymer of high electric charge density and it considerably swells in water and increases in stickiness, with the resulting difficulty in handling, even when it is cross-linked with a bifunctional cross-linking reagent.

In order to develop a polymeric membrane derived from maleic anhydride copolymer which can be used practically in an aqueous solution, the present inventor carried out a series of intensive studies, which led to the findings that the maleic anhydride copolymer becomes insoluble in water and swells only a little in water when it is blended with a support polymer and then partially cross-linked with a bifunctional cross-linking reagent. The present invention is based on these findings.

SUMMARY OF THE INVENTION

It is an object of the present invention to provide a polymeric membrane derived from maleic anhydride copolymer which is highly reactive and swells only a little in water.

It is another object of the present invention to provide a method for using the polymeric membrane as an ion exchange membrane by hydrolyzing the maleic anhydride residues in the membrane.

It is a further object of the present invention to provide a method for immobilizing an enzyme directly on or indirectly through an adequate spacer on the polymeric membrane.

The polymeric membrane of the present invention is composed of a blend of maleic anhydride copolymer and support polymer, the blend being partially cross-linked with a bifunctional cross-linking reagent.

The ion exchange membrane of the present invention is prepared by hydrolyzing the maleic anhydride residues of this polymeric membrane.

The enzyme immobilizing membrane of the present invention is prepared by bonding an enzyme immobilizing compound to the maleic anhydride residues of the polymeric membrane.

DESCRIPTION OF THE PREFERRED EMBODIMENTS

Since the polymeric membrane of this invention has maleic anhydride residues, it is possible to introduce easily functional groups into the membrane using the maleic anhydride residues.

The polymeric membrane of this invention is prepared by dissolving and mixing well (blending) a maleic anhydride copolymer and a support polymer in an organic solvent such as acetone, tetrahydrofuran, and acetonitrile, adding with vigorous agitation a bifunctional cross-linking reagent dissolved in the same organic solvent as above, and drying the solution slowly on a glass plate.

In blending, the quantity of maleic anhydride copolymer should be less than 50 wt. %, usually from 10 to 30 wt. %, and the quantity of support polymer should be more than 50 wt. %, usually from 70 to 90 wt. %. If the quantity of maleic anhydride copolymer in the blend is less than 10 wt. %, the membrane of this invention is low in permeability and reactivity due to insufficiency of maleic anhydride residues. On the other hand, if the quantity of maleic anhydride in the blend is more than 30 wt. %, the resulting membrane is low in strength during prepartion, drying, and storage. Examples of bifunctional cross-linking reagent include bifunctional compounds which are reactive with maleic anhydride residues, e.g., diamines and diols such as ethylenediamine, hexamethylenediamine, ethylene glycol, and propylene glycol. The bufunctional cross-linking reagent is used in an amount of 1/10 equivalent, usually from 1/20 to 1/5 equivalent, for the maleic anhydride residues. If the quantity of bifunctional cross-linking reagent is less than 1/20 equivalent, the resulting membrane is low in the degree of cross-linking and is poor in reproducibility of permeability. If it is more than 1/5 equivalent, clots are easy to occur during cross-linking. In other words, it is desirable that 5 to 20 mol. % out of the maleic anhydride residues in the blend should be cross-linked.

The maleic anhydride copolymer used in this invention is a copolymer of maleic anhydride and an olefin such as ethylene, propylene, and isobutene or a vinyl monomer such as vinyl acetate, allyl acetate, and isopropenyl acetate. The copolymer should preferably have a high molecular weight (usually 50,000 to 500,000). It is known that maleic anhydride usually forms a 1 to 1 copolymer with vinyl monomer. Therefore, the maleic anhydride residues in the copolymer are about 50 mol. %.

The support polymer should be such a polymer that can be formed into a membrane, does not react with the maleic anhydride copolymer, does not cause phase separation, and supports the maleic anhydride copolymer as a membrane. Thus, it is necessary to select a proper support polymer according to the kind of maleic anhydride copolymer.

The combination of maleic anhydride copolymer and support polymer should be as follows: Maleic anhydride-vinyl acetate copolymer or maleic anhydride-allyl acetate copolymer should preferably be combined with an alkyl methacrylate polymer such as poly(methyl methacrylate).

The polymeric membrane of this invention having maleic anhydride residues does not get wetted by water immediately after production. If the membrane, say 10 to 40 micron thick, is dipped in water for about 12 hours at room temperature, the maleic anhydride residues are hydrolyzed completely, and the membrane becomes ready for use as a cation exchange membrane. It is also possible to increase the permeability of the membrane by subjecting the membrane to an adequate alkali treatment. Further, it is also possible to prepare an amphoteric membrane having amino groups or a membrane having amino acids or acid azide groups, by reacting the membrane with a proper reagent in an aqueous solution, utilizing the fact that the maleic anhydride residues are more reactive with amines than with water and alcohol.

The polymeric membrane of this invention can be used as a material for immobilizing enzymes. In such a case, enzymes can be bonded directly to maleic anhydride residues on the membrane, or indirectly through a proper spacer or a functional group such as acid azide, diazonium, imide ester, aldehyde, acid chloride, isocyanate, and isothiocyanate which is commonly used for enzyme immobilization.

The invention is illustrated by the examples that follow.

EXAMPLE 1

<Preparation of polymeric membrane having maleic anhydride residues>

Solution A was prepared by dissolving 5 g of maleic anhydride-vinyl acetate copolymer having a molecular weight of about 120,000 in acetone sufficient to bring the total volume to 100 mL. Solution B was prepared by dissolving 5 g of commercial poly(methyl methacrylate) in acetone sufficient to bring the total volume to 100 mL. Solution C was prepared by dissolving 0.5 g of hexamethylene-diamine in acetone sufficient to bring the total volume to 100 mL. Three parts of solution A and 7 parts of solution B were mixed with thorough stirring, and the mixed solution was allowed to stand overnight at room temperature in a sealed container. One and a half parts of solution C was added dropwise to the mixed solution with vigorous agitation. Two milliliters of the resulting solution was spread on a flat Petri dish, 6 cm in diameter, and dried slowly at room temperature, with the cover on. A transparent membrane about $2.6 \times 10^{-3}$ cm thick was obtained.

EXAMPLE 2

<Conversion to cation exchange membrane>

(A) The polymeric membrane obtained in Example 1 was dipped in 0.1 N KOH aqueous solution and allowed to stand at room temperature for 12 hours. The membrane became turbid and slightly opaque. Even after complete washing with water, the membrane felt clammy due to the surface negative charge. The swelling was about 1.5 in the ratio of wet weight to dry weight (ph 5-10). The cation transport number of the treated membrane was determined to be about 0.96 by measuring the membrane potential for KCl solution in the range of 0.2M/0.02M to 0.04M/0.02M [1 mM tris(-hydroxylmethyl) aminomethane buffer solution, pH 8.0, 25° C.]. The membrane exhibited the permeability to glucose which is about one-fifth that of cellulose membrane.

(B) The polymeric membrane obtained in Example 1 was treated with 1 N KOH aqueous solution as above. The resulting membrane improved in permeability to glucose to about one half to one-third that of cellulose membrane (permeability coefficient $8 \times 10^{-7}$ cm$^3$/s). The permeability of negatively charged gluclose-6-phosphate is less than about 1/50 that of glucose, but it increases to ⅓ that of glucose if 5 mM Mg$^{2+}$ ions exist together and the negative charge is cancelled. It was demonstrated that the membrane treated as above has an ability to sieve molecules of the size of glucose by means of electrostatic effect. The cation transport number was 0.93 and 0.81 when the concentration of KCl was in the range of 0.04M/0.02M to 0.08M/0.02M and 0.08M/0.02M to 0.2M/0.02M, respectively. As regards the swelling ratio, the resulting membrane was not so different from the membrane treated in (A) above.

EXAMPLE 3

<Enzyme immobilizing membrane>

(A) Immobilization through acid azide;

The membrane obtained in Example 1 was dipped in 5% aqueous solution of hidrazine for 12 hours at room temperature. After thorough washing with water, the membrane was transferred into 30 mL of 2% aqueous solution of hydrochloric acid. (This treatment is preceded by alkali treatment where it is desirable to enlarge the pore diameter of the membrane.) While cooling with ice, 8 mL of 4% nitrous acid solution was added dropwise with vigorous agitation. Thus, an acid azidized membrane was obtained. This process is much faster than the conventional one to get the membrane acid azidized.

The resulting membrane was dipped in a 0.02M phosphate buffer solution (pH 7.4) containing 100 units of hexokinase (a product of Sigma Corp. U.S.) per 1 mL, at 4° C. for 12 hours with stirring. The membrane was washed thoroughly. The enzyme activity was found to be $1.9 \times 10^{-3}$ unit/cm$^3$, an enzyme leakage was not observed.

(B) Direct immobilization;

The polymeric membrane prepared in Example 1 was dipped in the hexokinase solution for 12 hours as in above (A). The resulting membrane was found to have the enzyme activity of $3.9 \times 10^{-4}$ unit/cm$^3$. When it comes to immobilizing an enzyme on the membrane surface, the process (A) which employs a spacer is superior to this process (B).

What is claimed is:

1. A polymeric membrane having maleic anhydride residues which comprise a blend of (1) a copolymer of maleic anhydride and an olefin or vinyl monomer and (2) a polyalkyl methacrylate, said blend being partially cross-linked with a bifunctional cross-linking reagent and being prepared by dissolving and mixing said copolymer and polyalkyl methacrylate in an organic solvent together with said bifunctional cross-linking reagent and thereafter removing the organic solvent.

2. A polymeric membrane as claimed in claim 1, wherein the bifunctional cross-linking reagent is a diamine or diol.

3. A polymeric membrane as claimed in claim 1, wherein the maleic anhydride copolymer and the support polymer are blended at a ratio of 10-30 : 70-90 (by weight).

4. A polymeric membrane as claimed in claim 1, wherein the quantity of the bifunctional cross-linking reagent is from 1/20 to 1/5 equivalent of maleic anhydride residues.

5. A polymeric membrane as claimed in any one of claims 1 to 4, wherein the maleic anhydride residues are connected to amino groups.

6. A polymeric membrane as claimed in any one of claims 1 to 4, wherein the maleic anhydride residues are connected to an enzyme.

7. A polymeric membrane as claimed in any one of claims 1 to 4, wherein the maleic anhydride residues are connected to an enzyme immobilizing compound selected from the group consisting of acid azide, imide ester, aldehyde, acid chloride, isocyanate, and isothiocyanate.

8. A polymeric membrane as claimed in claim 7, wherein the enzyme immobilizing compound is further connected to an enzyme.

* * * * *